United States Patent
Endo et al.

[11] Patent Number: 6,078,040
[45] Date of Patent: Jun. 20, 2000

[54] SMOKE DETECTING APPARATUS WITH A PREDETERMINED DIRECTION ELECTRIC FIELD COMPONENT

[75] Inventors: Ichiro Endo; Yukio Yamauchi, both of Tokyo, Japan

[73] Assignee: Hochiki Corporation, Tokyo, Japan

[21] Appl. No.: 09/107,285

[22] Filed: Jun. 30, 1998

[30] Foreign Application Priority Data

Jun. 30, 1997 [JP] Japan .................................. 9-173990

[51] Int. Cl.[7] ........................................................ G01V 8/00
[52] U.S. Cl. ........................ 250/222.2; 340/630; 356/340
[58] Field of Search .................................. 250/222.2, 574, 250/573; 340/630, 628, 629; 356/340, 336, 339

[56] References Cited

U.S. PATENT DOCUMENTS

| | | |
|---|---|---|
| 3,881,112 | 4/1975 | Roberts . |
| 5,319,575 | 6/1994 | Lilienfield ................................ 364/555 |
| 5,576,697 | 11/1996 | Nagashima et al. .................... 340/630 |

FOREIGN PATENT DOCUMENTS

| | | |
|---|---|---|
| 5-23709 | 4/1993 | Japan . |
| 609874 | 10/1948 | United Kingdom . |

*Primary Examiner*—Que T. Le
*Attorney, Agent, or Firm*—Sughrue, Mion, Zinn, Macpeak & Seas, PLLC

[57] ABSTRACT

A light source image, i.e., a near field pattern of the light-emitting face of a laser diode which emits laser light having the electric field component in a predetermined direction is formed by an imaging lens at an image forming position of a smoke detecting area through which a flow of sucked air passes. A light receiving device is disposed on an optical axis which passes through the image forming position of a light source image in the smoke detecting area and which is set in a plane that is substantially parallel to the direction of the electric field component of the laser light, and receives scattered light due to a smoke particle passing through the imaging position of the light source image and the vicinity of the imaging position.

6 Claims, 6 Drawing Sheets

| DIAMETER OF POLYSTYRENE LATEX PARTICLE | LIGHT RECEPTION PULSE LEVEL RATIO | |
|---|---|---|
| | PARALLEL TO ELECTRIC FIELD | PERPENDICULAR TO ELECTRIC FIELD |
| 0.3μm | 100 | 84.3 |
| 0.5μm | 100 | 45.0 |
| 1.0μm | 100 | 39.7 |

SMOKE DETECTING APPARATUS WITH A PREDETERMINED DIRECTION ELECTRIC FIELD COMPONENT

BACKGROUND OF THE INVENTION

1. Field of the Invention

The present invention relates to a smoke detecting apparatus which judges a fire by optically detecting smoke particles suspended in air sucked from a monitored zone, by means of laser light.

2. Description of the Related Art

Conventionally, a supersensitive smoke detecting apparatus is used in a computer room, a semiconductor manufacturing facility, or the like. In such a smoke detecting apparatus, the number of airborne particles (aerosol) including smoke particles suspended in air sucked from a monitored zone is optically detected by using laser light, and, when the particle number per unit time period exceeds a predetermined value, it is judged that a fire occurs.

Figure 8:
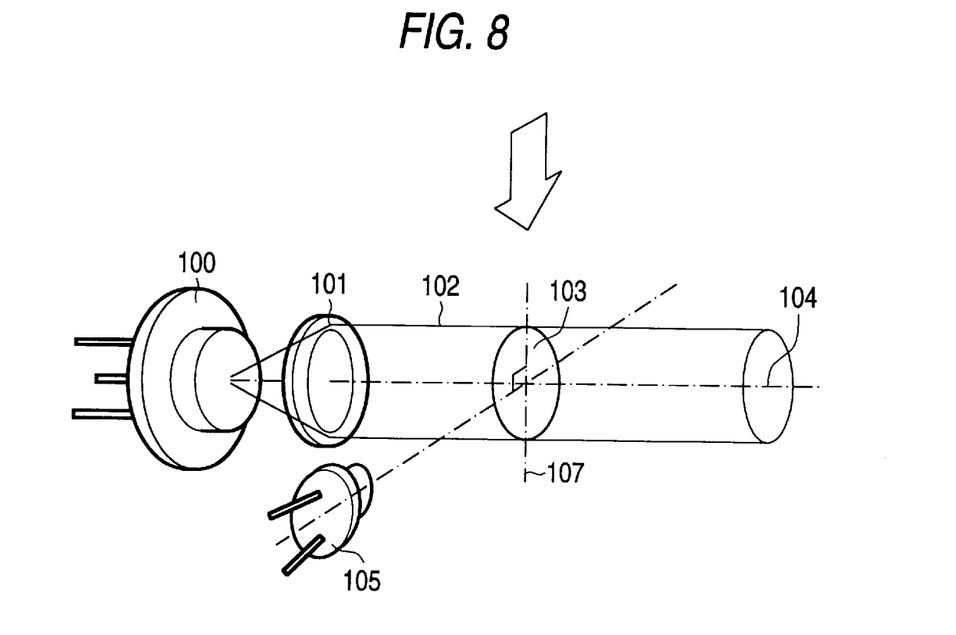
FIG. 8 is a diagram illustrating a smoke particle detecting structure of the scattered light type of the conventional art.

FIG. 8 shows an conventional apparatus. Such an apparatus is disclosed in, for example, Examined Japanese patent publication (Kokoku) No. HEI 5-23709. In the apparatus, laser light emitted from a laser diode 100 is converted into parallel beams 102 by a lens 101, and a smoke detecting area 103 through which sucked air passes is irradiated with the parallel beams. A light receiving device 105 is disposed in a direction perpendicular to an optical axis 104 of the parallel beams 102 which pass through the smoke detecting area 103, receives scattered light due to smoke particles passing through the smoke detecting area 103, and outputs a light reception pulse.

Figure 9:
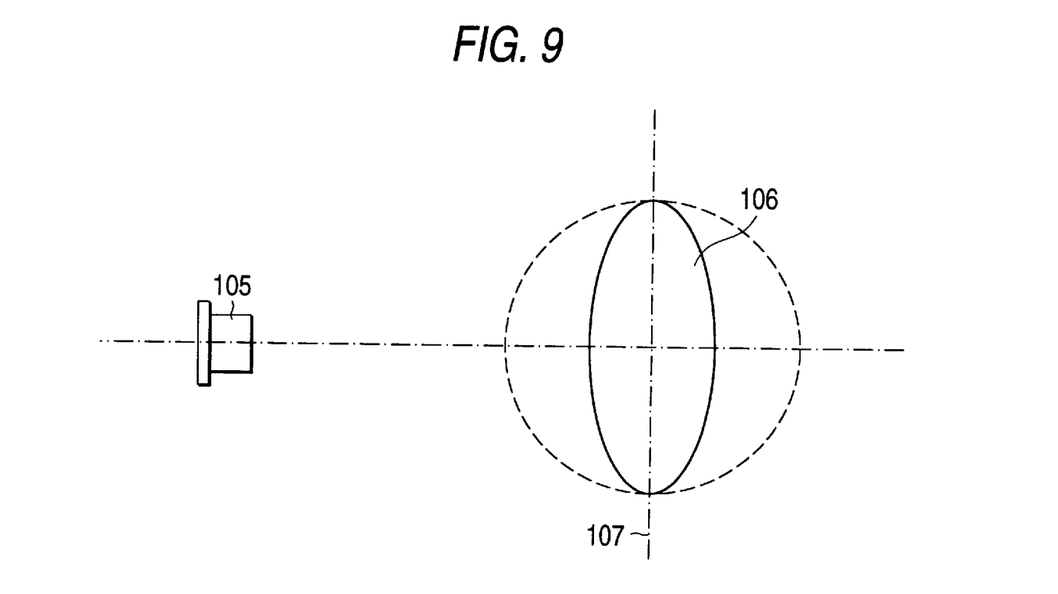
FIG. 9 is a diagram illustrating the direction of the disposition of a light receiving device with respect to an oval pattern of a smoke detecting area.

The light intensity distribution of the parallel beams passing through the smoke detecting area has an oval pattern 106 as shown in FIG. 9. It is known that the light emission pattern indicating the light intensity distribution in a sectional direction of laser light emitted from the laser diode 100 spreads in the form of an oval pattern. Also in the case where laser light is converted into the parallel beams 102, therefore, the light intensity distribution has the oval pattern 106 as shown in FIG. 7.

With respect to the light intensity distribution of the parallel beams 102 forming the oval pattern 106, in the prior art apparatus, the light receiving device 105 is disposed in a direction perpendicular to the major axis 107 of the oval pattern 106, thereby allowing scattered light due to smoke particles to be efficiently received.

Recently, as a result of advancement of the improvement of a laser diode, also a laser diode having a light emission pattern which is similar to a true circular pattern wherein the pattern of the major axis direction is identical with that of the minor axis direction has been developed. When a collimator lens is used as the lens 101 for converting laser light into the parallel beams 102, furthermore, diffuse light of an oval pattern from the laser diode can be efficiently converted into parallel beams of a true circular pattern.

Therefore, the parallel beams 102 passing through the smoke detecting area 103 as shown in FIG. 8 becomes closer to a substantially true circular pattern. As a result, the technique of the prior art in which the light receiving device is disposed in a direction perpendicular to the major axis 107 of the oval pattern 106 cannot be applied, thereby producing a problem in that the position where the light receiving device can receive scattered light with the highest efficiency cannot be determined.

SUMMARY OF THE INVENTION

It is an object of the invention to provide a smoke detecting apparatus in which a light receiving device can be disposed at a position where scattered light can be efficiently received irrespective of the light intensity distribution of laser light in a smoke detecting area, and which has so high resolution that light reception pulses can be detected so as to respectively correspond to smoke particles.

First, a smoke detecting apparatus of the present invention which determines a fire by optically detecting smoke particles suspended in air sucked from a monitored zone, has: a laser diode which emits laser light having an electric field component in a predetermined direction; an imaging lens which forms a light source image of a light-emitting face of the laser diode in a smoke detecting area through which sucked air passes; and a light receiving device which is disposed on an optical axis, the optical axis passing through an imaging position of the light source image in the smoke detecting area and being set in a plane which is substantially parallel to a direction of the electric field component of the laser light, the light receiving device receiving scattered light due to a smoke particle passing through the imaging position of the light source image and a vicinity of the imaging position in the smoke detecting area.

The present invention utilizes the property that the oval pattern of the light intensity distribution of laser light emitted from a laser diode is varied at a position remote from the emission face but not varied in the direction of the electric field component. Specifically, in the emission face of the laser diode, the light intensity distribution in a sectional direction perpendicular to the optical axis of laser light emitted from the laser diode has a laterally-elongating oval pattern called a near field pattern in which the major axis elongates in the lamination direction of the emission face and the minor axis elongates in a direction perpendicular to the lamination direction. As separating from the emission face of the laser diode, the beams are caused to spread by diffraction, so that the light intensity distribution has a vertically-elongating oval pattern called a far field pattern which is obtained by rotating the oval pattern of the near field pattern by 90 degrees.

Even when the direction of the oval pattern of the light intensity distribution is changed in the near and far field patterns, however, the direction of the electric field component is not changed. According to the invention, therefore, the electric field component of laser light emitted from the laser diode was checked by using a deflecting plate or the like. The light receiving device was disposed in a direction perpendicular to the optical axis of the imaging lens which passes through the imaging position of the smoke detecting area. Under this state, the light reception level at a constant smoke density was measured while changing the position of the light receiving device by revolving the light receiving device by 360 degrees about the optical axis. The measurement resulted in that the light reception level is highest when the light receiving device is disposed in a direction parallel to the deflection direction of laser light, and lowest when the light receiving device is disposed in a direction perpendicular to the deflection direction of laser light.

In the invention, therefore, a light receiving device which receives scattered light due to smoke particles is disposed on an optical axis which is substantially parallel to the direction of an electric field component of laser light. According to this configuration, scattered light due to smoke particles can be efficiently received irrespective of a physical pattern shape which shows the light intensity distribution of laser light in the smoke detecting area.

In this case, it is preferable to dispose the light receiving device on an optical axis which is substantially parallel to the direction of an electric field component of the laser light perpendicular to the optical axis of the imaging lens, because this configuration allows a smoke detecting mechanism to be miniaturized.

According to the invention, a light source image which is formed by the imaging lens is a near field pattern having an oval light intensity distribution which has a major axis elongating in the electric field direction and a minor axis elongating in a direction perpendicular to the electric field direction. The disposition of the light receiving device on the optical axis which is parallel to the direction of the electric field component of the laser light means that the light receiving device is disposed in the direction of the major axis of the near field pattern having an oval light intensity distribution.

According to the invention, furthermore, an image of the light-emitting face of the laser diode is formed by the imaging lens, into a spot-like shape in the smoke detecting area. Therefore, the smoke detecting area results in a minute spot area in which the light intensity is high, with the result that a light reception pulse due to scattered light which corresponds to each passage of a smoke particle can be efficiently detected.

Further, a smoke detecting apparatus which determines a fire by optically detecting smoke particles suspended in air sucked from a monitored zone, according to the present invention comprises: a laser diode which emits laser light having an electric field component in a predetermined direction to a smoke detecting area; a collimator lens which converts the light emitted from the laser diode to parallel light bundle; and a light receiving device receiving scattered light due to a smoke particle passing through the smoke detecting area at a position apart from the parallel light bundle, a receiving light axis of the light receiving device being disposed on a face substantially parallel to the electric field of the laser diode, the receiving light axis crossing the parallel light bundle at a predetermined angle.

In the above smoke detecting apparatus, a light source image formed by the collimator lens into the parallel light bundle is a near field pattern having an true-circular light intensity.

PREFERRED EMBODIMENT OF THE INVENTION

Preferred embodiment according to the present invention will be described as follows referring to the accompanying drawings.

Figure 1:
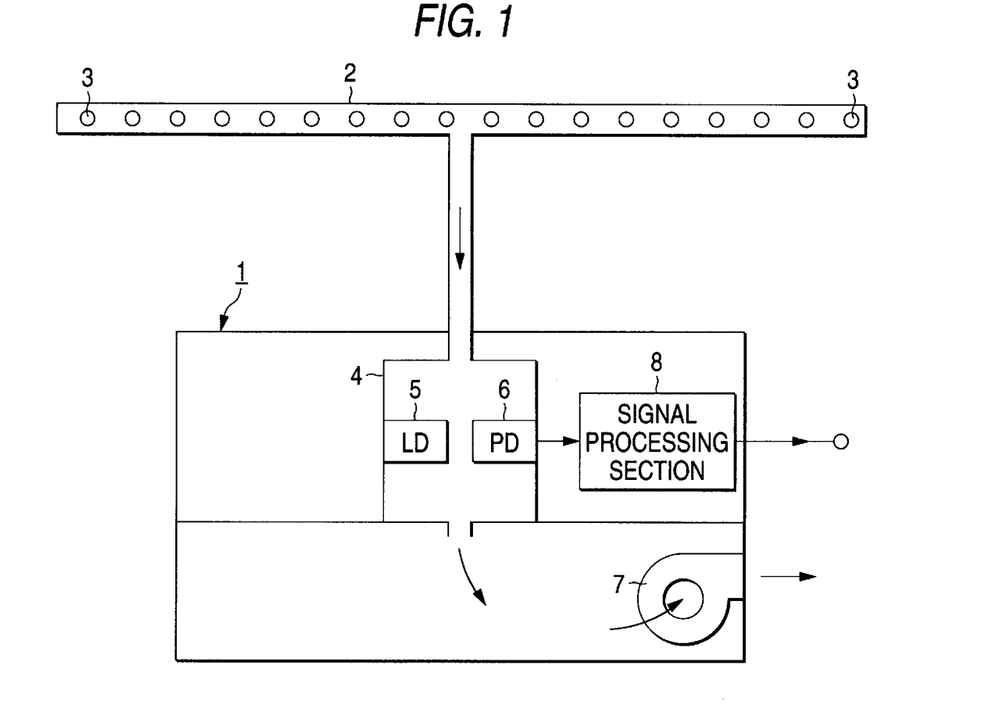
FIG. 1 is a diagram illustrating the whole configuration of the smoke detecting apparatus according to the invention.

FIG. 1 shows the whole configuration of the smoke detecting apparatus of the invention. Referring to FIG. 1, the smoke detecting apparatus 1 is installed in a computer room, a clean room in which semiconductor manufacturing equipment is disposed, or the like. A detecting pipe 2 disposed in a monitored zone is connected to the smoke detecting apparatus 1. For example, the detecting pipe 2 is a T-shaped pipe having a plurality of suction holes 3.

The detecting pipe 2 is connected to an inlet of a smoke detecting section 4 disposed in the smoke detecting apparatus 1, and an outlet side is opened in a chamber provided with a sucking device 7. In a monitoring state, the sucking device 7 is driven by a motor so as to suck air of a predetermined flow rate. Accordingly, the air which is once sucked through the suction holes 3 of the detecting pipe 2 disposed in a security zone is discharged from the sucking device 7 through the smoke detecting section 4.

The smoke detecting section 4 has a laser diode (LD) which serves as a light-emitting device and performs single-deflection oscillation, and a photodiode (PD) 6 serving as a light receiving device. The photodiode 6 is, for example, a PIN photodiode.

Airborne particles (aerosol) including smoke particles existing in the sucked air which passes through the smoke detecting section 4 are detected in the following manner. Scattered light caused by laser light radiation from the laser diode 5 is detected by the photodiode 6. A light reception pulse signal corresponding to the scattered light is supplied to a signal processing section 8. The signal processing section 8 processes the light reception pulse signal due to the scattered light which is obtained from the photodiode 6 for each smoke particle, so as to count, for example, the number particles per unit time period, and converts the number into the smoke density. When the smoke density exceeds a predetermined threshold value, it is judged that a fire occurs, and a fire detection signal is output to the outside.

The size of a smoke particle to be detected is predetermined to be, for example, 0.3 to 1.0 $\mu$m. Therefore, the signal processing section 8 may extract a light reception pulse signal from the photodiode 6 which corresponds to the range of the particle diameter, to count smoke particles, and, when the smoke density exceeds the threshold value, it may be judged that a fire occurs.

Figure 2:
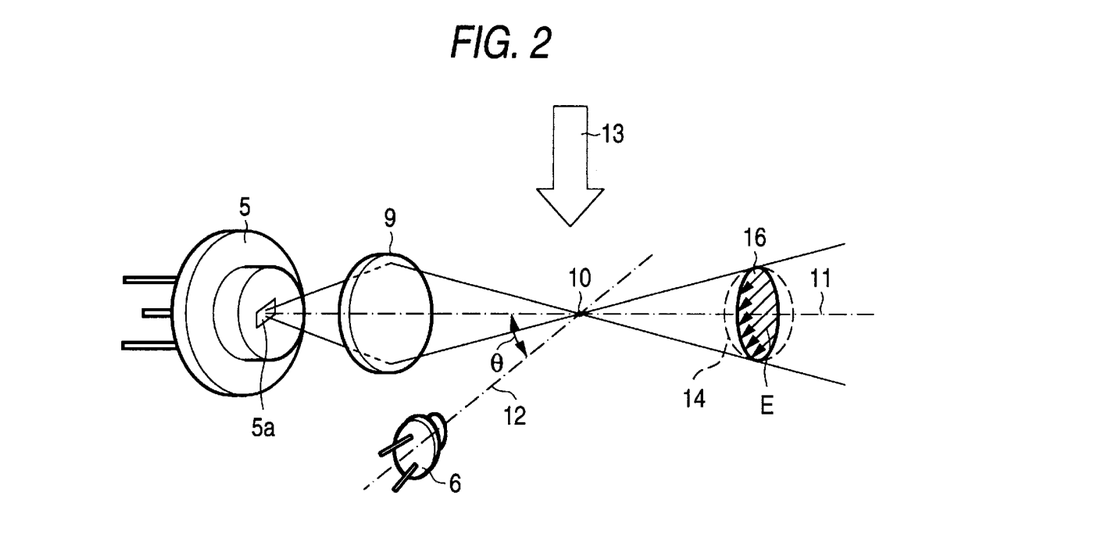
FIG. 2 is a diagram illustrating a smoke particle detecting structure of the scattered light type according to the invention.

FIG. 2 is a diagram illustrating a smoke particle detecting structure of the scattered light type according to the invention and disposed in the smoke detecting section 4 shown in FIG. 1. Referring to FIG. 2, the laser diode 5 performs so-called single-deflection oscillation in which the electric field of the emitted laser light is determined in a predetermined direction, and incorporates a laser diode chip 5a. The laser light emitted from the laser diode 5 spreads as a diffusion wave as propagating in the direction of a projection optical axis 11.

Subsequent to the laser diode 5, an imaging lens 9 is disposed at a predetermined position in the projection optical axis 11. The imaging lens 9 converges the laser light from the laser diode 5 to form a light source image of a light-emitting face of the laser diode chip 5a of the laser diode 5, at an imaging position 10 through which an air flow 13 passes.

At the imaging position 10 of the light source image of the laser diode 5 which is formed by the imaging lens 9, the photodiode 6 is disposed so as to have a reception optical axis 12 which elongates in, for example, a direction perpendicular to the projection optical axis 11. The photodiode 6 is-disposed on the reception optical axis 12 parallel to a direction of an electric field E indicated by arrows in an oval far field pattern 16 which shows the light intensity distribution in an optical axis sectional direction of laser light which diffuses beyond the imaging position 10.

Figure 3A:
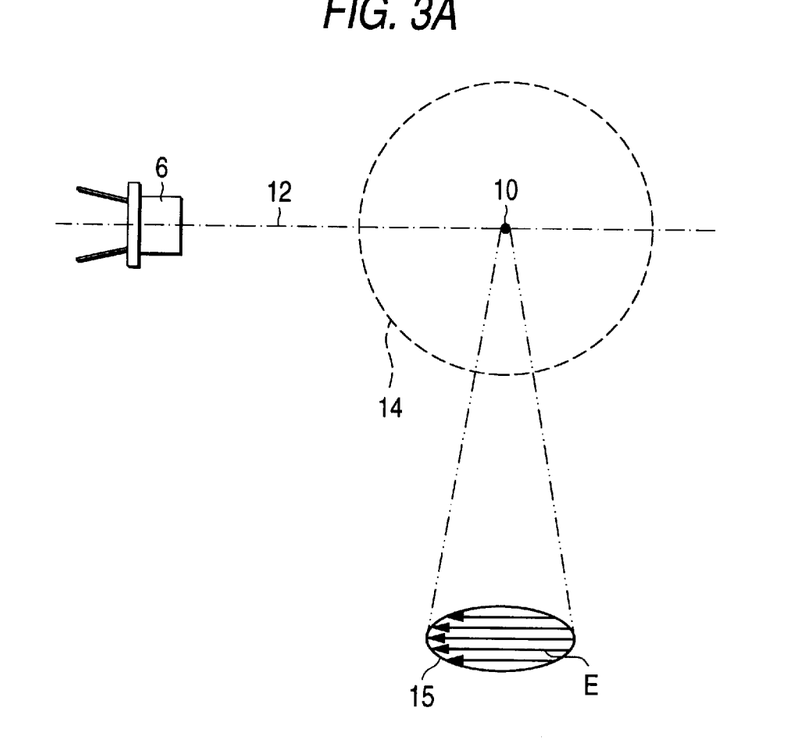
FIGS. 3A and 3B are diagrams illustrating a light intensity distribution pattern and an electric field direction at an imaging position of FIG. 2 and a position separated from the imaging position.
Figure 3B:
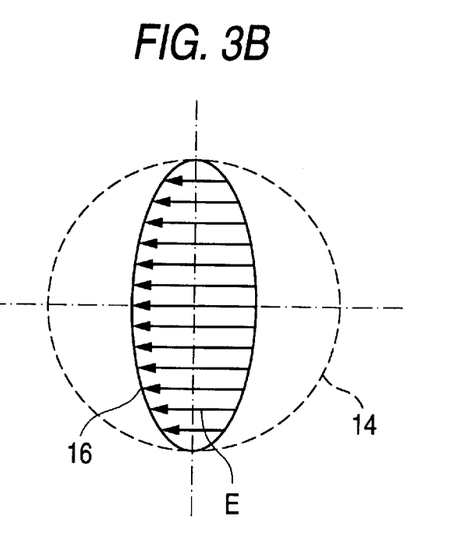

FIG. 3(A) shows the imaging position of FIG. 2 in a sectional direction of the projection optical axis 10. The light source image of the laser diode 5 at the imaging position 10 is enlargedly shown in the lower side. FIG. 3(B) shows the oval far field pattern 16 and the direction of the electric field E in a section of the projection optical axis 11 which is positioned beyond the imaging position 10 of FIG. 2, and also a true circular pattern 14 indicated by a broken line.

Figure 4:
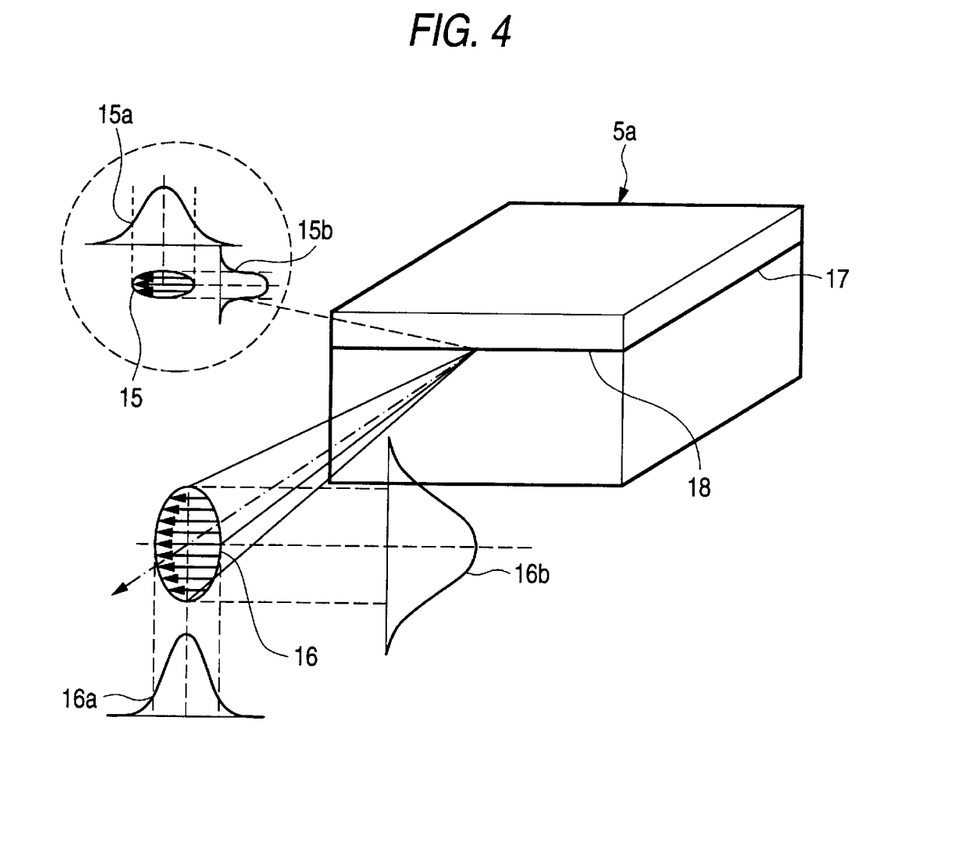
FIG. 4 is a diagram illustrating near and far field patterns of a laser diode.

For example, the light intensity distribution and the electric field of laser light emitted from the laser diode chip 5a of FIG. 2 are as shown in FIG. 4. FIG. 4 shows the laser diode chip 5a in an enlarged manner. Laser light is emitted from a light-emitting face 18 which is positioned in front of an active layer 17 known as an oscillation area. The laser light is a diffusion wave which spreads as forward separating from the light-emitting face 18.

In the diffusion wave from the emitting face 18, a near field pattern 15 which shows the light intensity distribution in the light-emitting face 18 in a direction perpendicular to the optical axis is a laterally-elongating oval pattern in which the width of the vertical transverse mode 15b is smaller than that of the horizontal transverse mode 15a.

Beams are caused to spread as separating from the light-emitting face 18, by diffraction of laser light. At a position separated from the face by a certain distance, therefore, the near field pattern 15 is changed to a far field pattern 16 which is obtained by rotating the near field pattern 15 by 90° or which is a vertically-elongating oval pattern.

In contrast to the near field pattern 15, in the far field pattern 16, the horizontal transverse mode 16a has a smaller width and the vertical transverse mode 16b has a larger width.

By contrast, the direction of the electric field of laser light from the laser diode chip 5a is a lateral direction in the figure which is parallel to the active layer 17. The direction of the magnetic field is perpendicular to that of the electric field. Usually, deflection is indicated by the propagation direction of the electric field. The deflection direction of laser light can be easily known by using a deflecting plate.

In the embodiment of FIG. 2, therefore, laser light emitted from the laser diode 5 is checked by using a deflecting plate to know the polarization direction of the electric field E, and the photodiode 6 is disposed so that the reception optical axis 12 elongates in parallel to the polarization direction and passes through the imaging position 10 of the imaging lens 9. The light source image of the laser diode 5 which is formed at the imaging position 10 by the imaging lens 9 is an optical image of the near field pattern 15 of the light-emitting face 18 shown in FIG. 4.

Referring to FIG. 3(A), at the imaging position 10, in the embodiment, the lateral direction coincides with the polarization direction of the electric field, as shown in the enlarged near field pattern 15, and an oval pattern which elongates in the polarization direction of the electric field is obtained. When the disposition direction of the light receiving device 6 is defined in the oval pattern showing the light intensity distribution of the near field pattern 15 which is formed as a light source image at the imaging position 10, therefore, it will be seen that the photodiode 6 is disposed with setting the reception optical axis 12 to elongate in parallel to the major axis direction of the oval pattern in the near field pattern 15.

Figure 5:
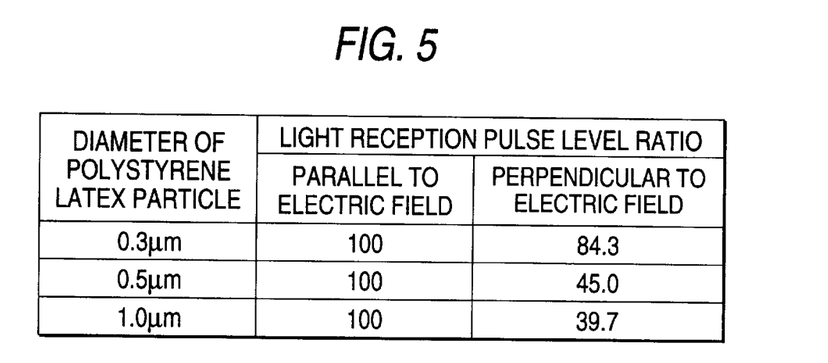
FIG. 5 shows measurement results of a light reception pulse signal with respect to a change of the particle diameter in the case of a direction parallel to the electric field in the invention, and the case of a direction perpendicular to the electric field in a comparison example.
Figure 6:
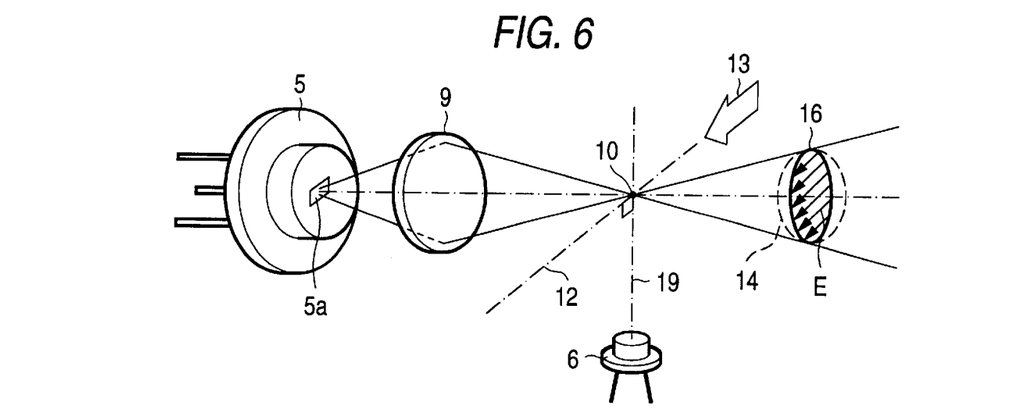
FIG. 6 is a diagram illustrating a case where a light receiving device is disposed in a direction perpendicular to the electric field direction in FIG. 2.

FIG. 5 shows level ratios of light reception pulse signals in the case where, as the embodiment of FIG. 2, the photodiode 6 was disposed in a direction parallel to the electric field direction of the laser diode 5, and that where, as a comparison example of FIG. 6, the photodiode 6 was disposed with setting the reception optical axis 19 to elongate in a direction perpendicular to the direction of the electric field E of the laser diode 5. In these cases, polystyrene latex particles were used as artificial smoke particles.

Figure 7A:
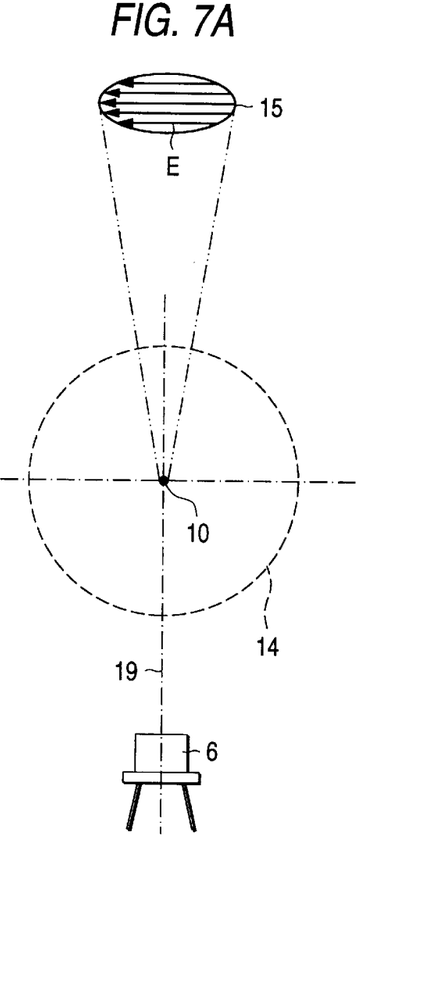
FIGS. 7A and 7B are diagrams illustrating a light intensity distribution pattern and an electric field direction at an imaging position of FIG. 6 and a position separated from the imaging position.
Figure 7B:
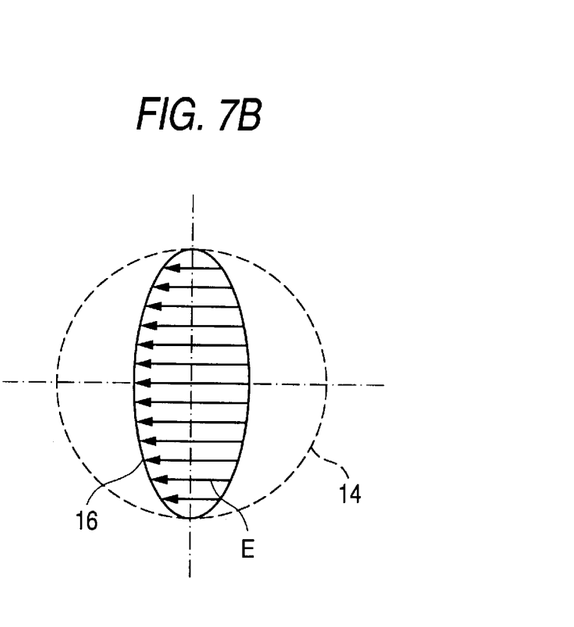

In the comparison example of FIG. 6, in the plane perpendicular to the optical axis at the imaging position 10 of the imaging lens 9 in FIG. 7(A), the light receiving device 6 is disposed in direction of the reception optical axis 19 perpendicular to the electric field direction E of the near field pattern 15 which is the light source image of the laser diode 5 obtained by magnifying the imaging position 10. FIG. 7(B) shows the far field pattern 16 in the comparison example of FIG. 6 and beyond the imaging position 10, in the same manner as FIG. 3(B).

In the embodiment of the invention of FIG. 2 and the comparison example of FIG. 6, the level of the light reception pulse signal of the photodiode 6 was measured while polystyrene latex particles of three kinds of particle diameters, i.e., 0.3 μm, 0.5 μm, and 1.0 μm shown in FIG. 5 were passed along the air flow 13 through the smoke detecting area including the imaging position 10. The light reception pulse levels in the comparison example of FIG. 6 are indicated as measurement results while the light reception pulse levels in the invention of FIG. 2 are indicated as 100.

As apparent from the measurement results of FIG. 5, with respect to all the particle diameters, the light reception pulse levels in the comparison example in which the light receiving device is disposed in a direction perpendicular to the electric field are lower than those of the embodiment of the invention in which the light receiving device is disposed in a direction parallel to the electric field. Specifically, when the particle diameter is 0.3 μm, the level in the case where the device is disposed in perpendicular to the electric field is 84.3 as compared with the case where the device is disposed in parallel to the electric field. When the particle diameter is increased to 0.5 μm, the level in the case where the device is disposed in perpendicular to the electric field is reduced to 45.0 or one half or less the level of 100 in the case where the device is disposed in parallel to the electric field. When the particle diameter is further increased to 1.0 μm, the level in the case where the device is disposed in perpendicular to the electric field is reduced to 39.3 or about one third the level of 100 in the case where the device is disposed in parallel to the electric field.

As a result, in the particle diameter range of 0.3 to 1.0 μm, the disposition of the photodiode 6 in a direction parallel to the electric field as in the embodiment of the invention of FIG. 2 increases the received amount of scattered light due to smoke particles, as compared with the case where the device is disposed in perpendicular to the electric field, and enables light reception pulses to be obtained with the highest efficiency.

The disposition direction of the light receiving device 6 in the embodiment of FIG. 2 is not restricted to the one which is perfectly parallel to the direction of the electric field E. When the disposition direction is within a range of, for example, about plus and minus ten and several degrees with respect to the direction parallel to the electric field E, the light reception pulse signal can be detected more efficiently as compared with the case of a perpendicular direction.

In the embodiment of FIG. 2, the angle θ formed by the reception optical axis 12 elongating in parallel to the electric field E of the laser light from the laser diode 5 and passing through the imaging position 10, and the projection optical axis 11 is set to be θ=90° or a right angle. Because of θ=90°, the smoke particle detecting structure of the scattered light type which is composed of the laser diode 5, the imaging lens 9, and the photodiode 6 can be compactly produced or miniaturized.

If necessary, the intersection angle θ between the projection optical axis 11 and the reception optical axis 12 may be changed to a value other than 90°. In this case, when the intersection angle θ is smaller than 90°, the photodiode 6 is excessively close to the imaging lens 9 so that the disposition space has no margin. Therefore, it is preferable to set the intersection angle θ to be 90° or more so that the photodiode 6 is separated from the imaging lens 9, thereby improving the assembling property. In the above embodiment, although the intersection angle θ is set to be 90° due to the structural reason, it is preferable to set to be 100° to 120°. However, even if the intersection angle θ is set to be 60° to 100°, it has sufficient effect of the present invention.

In the embodiment of FIG. 2, the flow 13 of the air sucked from a monitored space is passed through the imaging position 10 of the imaging lens 9 from, for example, the upper side. The position where light collides with smoke particles to be scattered is restricted to the area of the near field pattern 15 formed as the light source image at the imaging position 10, and the near field pattern 15 itself is an area of the order of micrometers. Consequently, among smoke particles having a particle diameter of 0.3 to 1.0 μm such as shown in FIG. 5, the number of particles which can pass through the area at any instance is restricted to about one. For one smoke particle, therefore, the photodiode 6 can output one light reception pulse. As compared with the case of parallel beam in the prior art of FIG. 8, the detection resolution for smoke particles can be largely enhanced.

Figure 10:
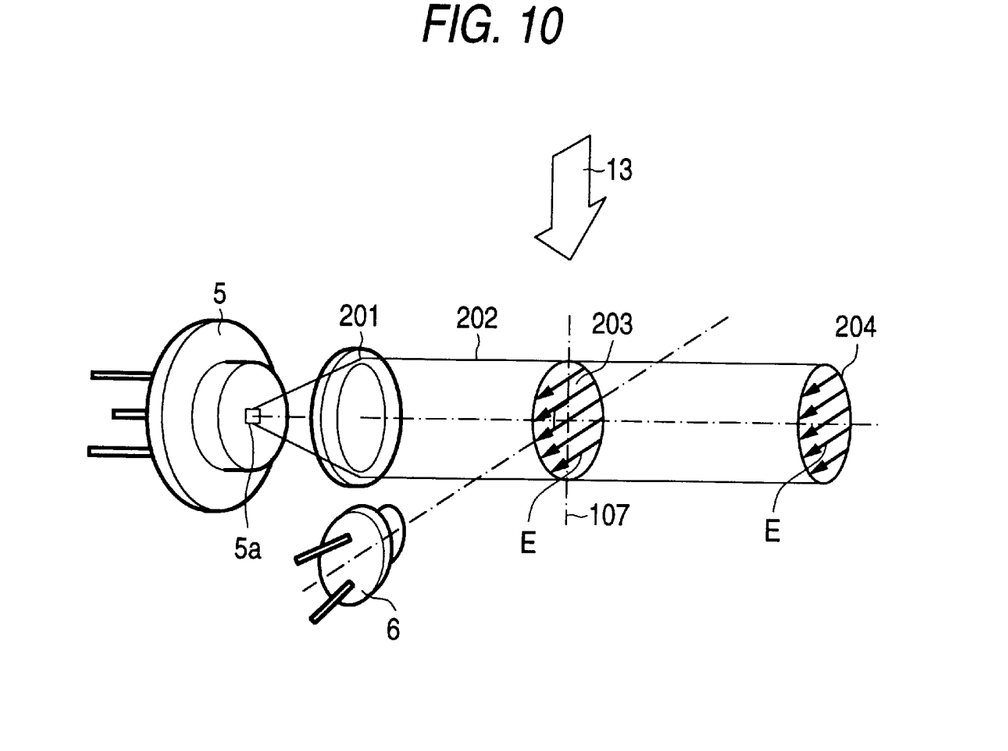
FIG. 10 is a diagram showing another example of a smoke particle detecting structure of the scattered light type according to the invention.

In the above-described embodiments, as shown in FIG. 2, the laser light from the laser diode 5 is confined to the imaging position 10 by the imaging lens 9, so as to form a light source image of a minute beam spot. The air flow of smoke particles sucked from the outside is caused to pass through the beam spot of the imaging position. Alternatively, the invention may be applied as it is to a smoke detecting apparatus provided with a parallel-light optical system as shown in FIG. 10. In the parallel-light optical system, a collimator lens 201 is used instead of the imaging lens 9, the laser light from the laser diode 5 is converted into parallel light, and the photodiode 6 serving as a light receiving device is disposed so as to form a predetermined configuration angle θ with respect to the parallel light. Incidentally, reference numeral 203 is a true-circular detecting smoke detecting area and 204 is a true-circular pattern. In this case, the collimator lens 201 also has a true-circular shape.

As described above, according to the invention, a light receiving device is disposed on an optical axis passing through an imaging position of the light source image (near field pattern) of a laser diode formed by an imaging lens in the smoke detecting area, and set in a plane which is substantially parallel to a direction of an electric field component of the laser light. Scattered light due to a smoke particle passing through the imaging position of the light source image and the vicinity of the imaging position is received. Accordingly, scattered light due to smoke particles can be efficiently received irrespective of a physical oval pattern shape which shows the light intensity distribution of laser light in the smoke detecting area. The smoke particles can be counted on the basis of light reception pulses, and a fire can be judged.

According to the invention, a light source image (near field pattern) of the light-emitting face of the laser diode is formed in the smoke detecting area by the imaging lens, thereby forming a minute spot area of the order of micrometers. Therefore, a light reception pulse due to scattered light which corresponds to each smoke particle passing through the imaging position can be correctly detected, and the S/N ratio can be improved.

What is claimed is:

1. A smoke detecting apparatus which determines a fire by optically detecting smoke particles suspended in air sucked from a monitored zone, comprising:

a laser diode which emits laser light having an electric field component in a predetermined direction;

an imaging lens which forms a light source image of a light-emitting face of said laser diode in a smoke detecting area through which sucked air passes; and a light receiving device which is disposed on an optical axis, said optical axis passing through an imaging position of the light source image in said smoke detecting area and being set in a plane which is substantially parallel to a direction of the electric field component of the laser light, said light receiving device receiving scattered light due to a smoke particle passing through the imaging position of the light source image and a vicinity of the imaging position in said smoke detecting area.

2. A smoke detecting apparatus according to claim 1, wherein an optical axis of said light receiving device is set to elongate in a direction perpendicular to an optical axis of the laser light in the plane which passes through the imaging position of the light source image in said smoke detecting area and which is substantially parallel to the direction of the electric field component of the laser light.

3. A smoke detecting apparatus according to claim 1, wherein the light source image formed by said imaging lens is a near field pattern having an oval light intensity distribution which has a major axis elongating in the electric field direction and a minor axis elongating in a direction perpendicular to the electric field direction.

4. A smoke detecting apparatus according to claim 1, wherein an optical axis of said light receiving device is set to elongate in a direction of a major axis of the near field pattern having an oval light intensity distribution.

5. A smoke detecting apparatus which determines a fire by optically detecting smoke particles suspended in air sucked from a monitored zone, comprising:

a laser diode which emits laser light having an electric field component in a predetermined direction to a smoke detecting area;

a collimator lens which converts the light emitted from the laser diode to parallel light bundle; and a light receiving device receiving scattered light due to a smoke particle passing through the smoke detecting area at a position apart from the parallel light bundle, a receiving light axis of the light receiving device being disposed on a face substantially parallel to the electric field of the laser diode, the receiving light axis crossing the parallel light bundle at a predetermined angle.

6. A smoke detecting apparatus according to claim 5, wherein a light source image formed by the collimator lens into the parallel light bundle is a near field pattern having an true-circular light intensity.

* * * * *